US006556293B2

(12) United States Patent
Savareigo

(10) Patent No.: US 6,556,293 B2
(45) Date of Patent: Apr. 29, 2003

(54) OPTICAL INSPECTION OF LASER VIAS

(75) Inventor: Nissim Savareigo, Ashdod (IL)

(73) Assignee: Orbotech Ltd., Yavne (IL)

( * ) Notice: Subject to any disclaimer, the term of this patent is extended or adjusted under 35 U.S.C. 154(b) by 0 days.

(21) Appl. No.: 09/825,493

(22) Filed: Apr. 3, 2001

(65) Prior Publication Data

US 2001/0028454 A1 Oct. 11, 2001

(30) Foreign Application Priority Data

Apr. 6, 2000 (IL) .................................................. 135522

(51) Int. Cl.$^7$ ................................................ G01N 21/88
(52) U.S. Cl. ............................. 356/237.5; 356/237.4; 356/237.2
(58) Field of Search ............... 356/71, 73, 237.1–237.6, 356/390, 394; 250/453.11, 458.1, 559.03, 559.41, 559.42, 559.45, 271, 226; 235/462, 468

(56) References Cited

U.S. PATENT DOCUMENTS

| 4,166,540 A | * | 9/1979 | Marshall ....................... 356/71 |
| 4,983,817 A | * | 1/1991 | Dolash et al. ................ 250/271 |
| 5,127,730 A | * | 7/1992 | Brelje et al. ................. 356/318 |
| 5,608,225 A | * | 3/1997 | Kamimura et al. ........ 250/458.1 |
| 5,773,808 A | * | 6/1998 | Lase ........................... 235/462 |
| 5,903,342 A | * | 5/1999 | Yatsugake et al. ......... 356/237.4 |
| 6,033,503 A | * | 3/2000 | Radowicz et al. ........ 250/458.1 |

FOREIGN PATENT DOCUMENTS

WO        WO00/09993        2/2000

* cited by examiner

*Primary Examiner*—Michael P. Stafira
*Assistant Examiner*—Sang H. Nguyen
(74) *Attorney, Agent, or Firm*—Ladas & Parry

(57) ABSTRACT

An automated optical inspection system including a source of electromagnetic radiation for delivering a radiation beam on an article to be inspected, a plurality of sensors arranged with respect to the radiation beam for sensing a plurality of radiation properties associated with the radiation beam impinging at least at a zone of impingement on a substance found on the article to be inspected, the plurality of sensors including a luminescence sensor for sensing luminescence of the substance due to the beam impinging thereon and a reflectance sensor for sensing reflectance of the beam from the substance the sensors transmitting information signals based on the radiation properties sensed by the sensors and a processor in communication with the sensors operative to receive the information signals for a plurality of zones of impingement, to combine the signals from the sensors and to analyze them, and to generate an output indicating the presence of defects based on the analysis.

41 Claims, 9 Drawing Sheets

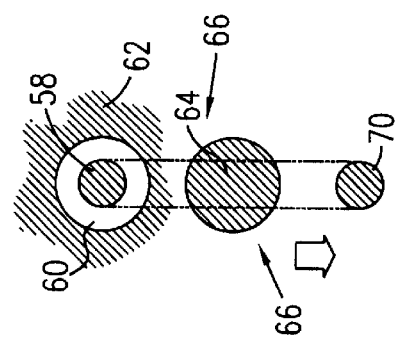
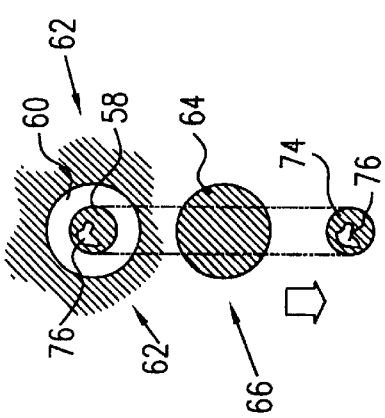
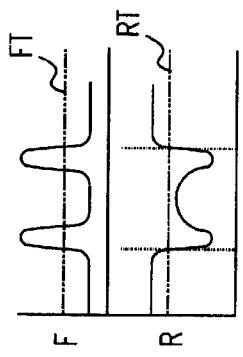
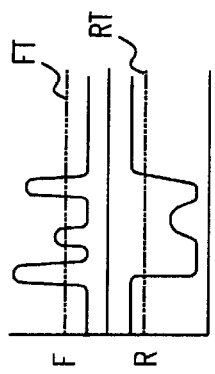
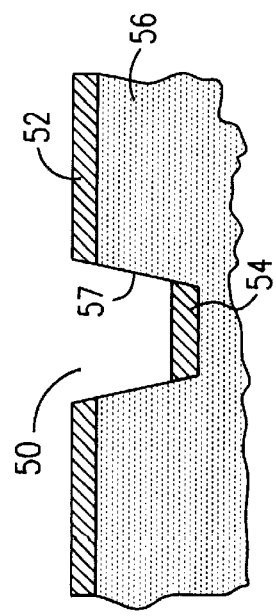
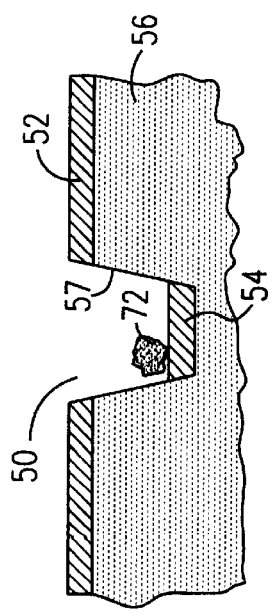

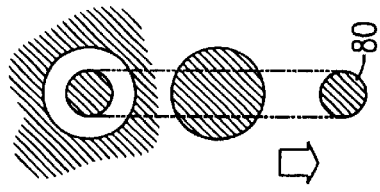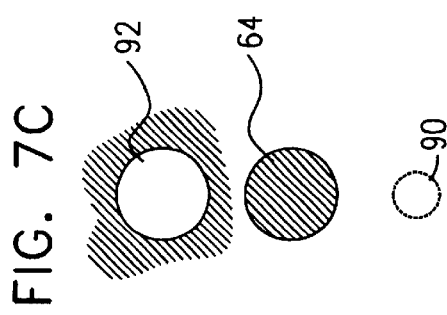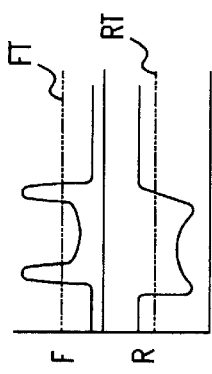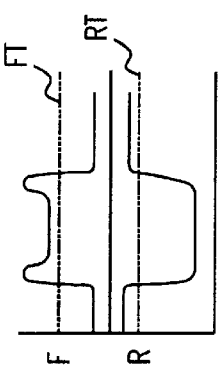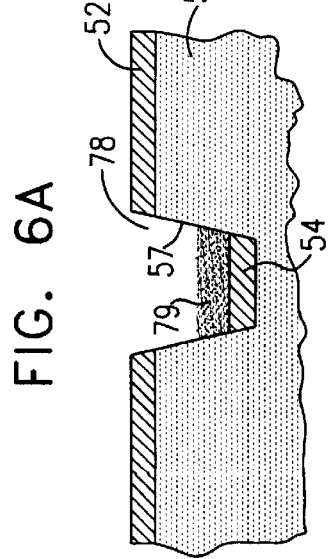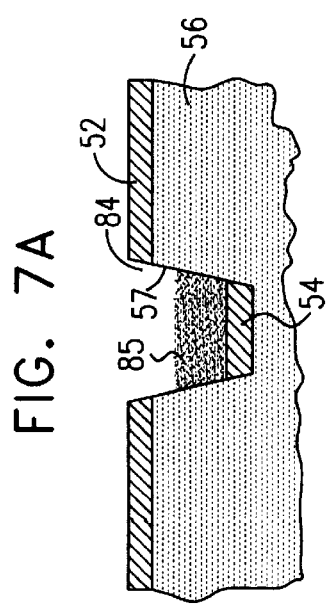

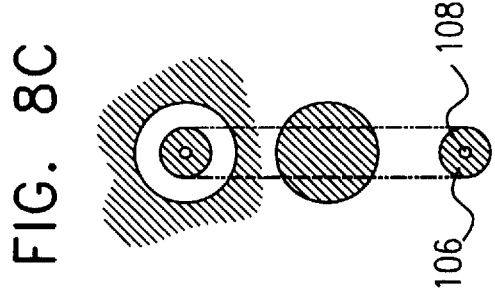
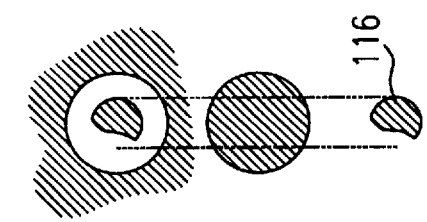
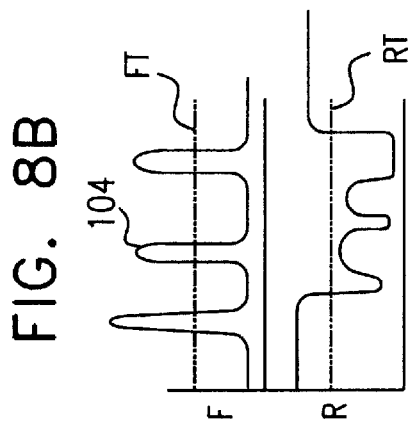
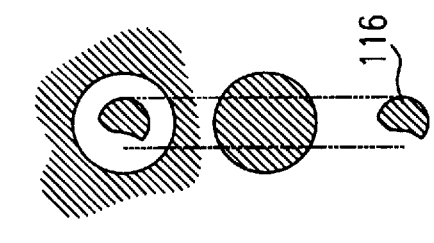
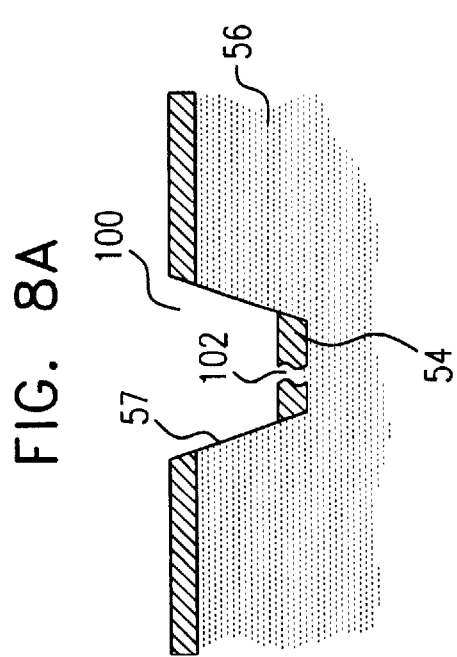
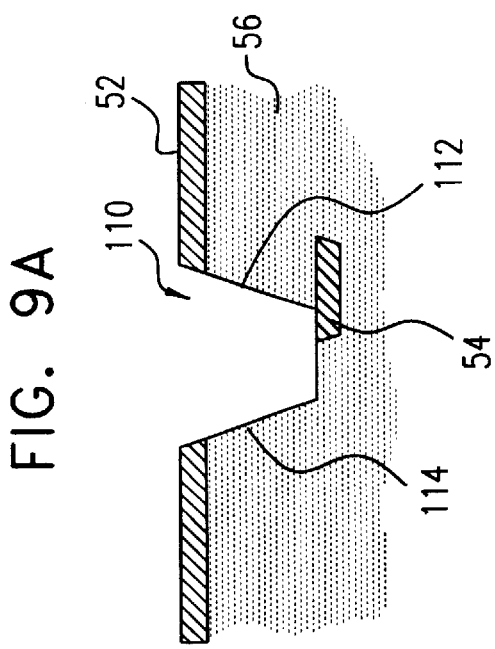

OPTICAL INSPECTION OF LASER VIAS

FIELD OF THE INVENTION

The present invention relates generally to automated optical inspection (AOI) systems and particularly to an AOI system for inspecting and detecting defects in laser-drilled vias in printed electrical circuits.

BACKGROUND OF THE INVENTION

Most multi-layer printed circuit boards ("PCB"s) have vias, i.e., passageways from one layer to another, which generally are plated to provide electrical contact between the layers. Vias may be formed in many ways, for example by means of apertures in the required x–y positions in each layer, such that when the layers are joined together one on top of another and properly registered, the apertures define the via path.

Recently vias have been made by first forming a laminated multi-layer board, and then by drilling the vias by means of photoablating and/or photo-cutting with a laser beam. Two examples of widely used lasers are frequency tripled (or quadrupled) pulsed YAG lasers (wavelength 355 or 266 nm) and $CO_2$ lasers (wavelength about 10.6 $\mu$m). Both types of lasers can easily cut PCB laminate materials, such as glass-epoxy or polyimide. These two types of lasers have different advantages and disadvantages. For example, the laser beam of a YAG laser cuts through copper. This characteristic offers the advantage of being able to use a YAG laser to prepare vias on substrates that are coated with copper, however one can overdrill the laminate (insulating layer) into the copper of the lower layer if precautions are not taken. Conversely, the laser beam of a $CO_2$ laser does not cut through the copper, thus there is no danger of overdrilling. However a $CO_2$ laser can not be used to prepare vias on substrates coated with copper. Consequently, when a $CO_2$ laser is used, metal must be removed from the top layer where it is desired to drill a via, for example by etching, which does not have to be done for a YAG laser.

FIGS. 1A–1F illustrate different typical defects associated with laser-drilled vias. The figures show an upper copper layer 2, a laminate layer 3 and a lower copper pad 4, wherein it is desired to drill a via 5 from upper layer 2 down to the top of pad 4. FIG. 1A illustrates an underdrilled via, which of course means that although the via is plated with copper, no electrical connection will be made between layer 2 and pad 4. FIG. 1B illustrates an overdrilled via, which means that the via is drilled through pad 4 resulting in too little metal being left on pad 4 for a reliable electrical connection between layer 2 and pad 4. FIG. 1C illustrates "throw out", i.e., debris 6 from photoablation of the layers being left in via 5, which can cause plating or electrical connection problems. FIG. 1D illustrates the presence of foreign materials 7 in the via, which can cause plating or electrical connection problems. FIG. 1E illustrates an underplated via, namely a properly drilled via having plating 8 that is not suitably deposited which can lead to an insufficient electrical connection. FIG. 1F illustrates via 5 misregistered with pad 4, which, although not being a defect in the drilling process per se, nevertheless is a defect which must be detected because it too can lead to an insufficient electrical connection.

Although automated optical inspection (AOI) systems are typically used to inspect PCBs, nevertheless no AOI system is known which can accurately, repeatably and reliably detect various defects in laser-drilled vias, independently of whether or not the PCB under inspection, and the vias thereon, are cleaned prior to inspection. Moreover no laser drill repair station is known to inspect substantially all laser drill vias on a PCB and to automatically repair only those defective laser drill vias having defect types that are repairable.

U.S. Pat. No. 5,216,479 shows and describes an optical inspection system for inspecting a surface of a laminate operative to distinguish between a first material, such as a printed circuit board laminate, and a second material, such as copper formed thereon, and employing a laser illuminator selectively illuminating the surface and signal analyzers operative to sense and analyze fluorescent light and reflected light resulting from illumination by the laser.

SUMMARY OF THE INVENTION

The present invention seeks to provide a novel AOI system which can accurately, repeatably and reliably detect and distinguish various different defects in laser-drilled vias. The present invention can simultaneously inspect through holes and laser-drilled vias. Preferably the detection of the various different defects can be made independently of whether or not the PCB under inspection, and the vias thereon, are cleaned prior to inspection.

Additionally, the present invention seeks to provide a novel AOI system which can accurately, repeatably and reliably detect and distinguish various different defects in laser-drilled vias, and which can automatically repair, for example by redrilling, those defective vias which are repairable. Preferably, if non-repairable defects are detected then no vias, such as vias having repairable defects, are redrilled.

The present invention uses a combination of inputs from at least two optical data channels which sense one or more of three different parameters of a radiation beam impinging on substances found on the PCB: luminescence of the substance (laminate, copper layer, copper pad, debris, etc.) due to the beam impinging thereon, reflection of the beam from the substance, and transmission of the beam at the point of impingement. Each data channel preferably is adjustable independently of the other channels for optimal performance. Although most preferably the beam is a laser beam, nevertheless the invention can be carried out with any coherent or non-coherent monochromatic or polychromatic light beam, or any other radiation, electromagnetic wave or acoustic beam, for example.

It is noted that the term "luminescence" refers to the emission of visible or non-visible electromagnetic radiation as a result of absorption of exciting energy in the form of photons, charged particles, or chemical change. The term luminescence includes both fluorescence and phosphorescence. In "fluorescence", an atom or molecule emits detectable radiation in passing from a higher to a lower electron excitation state. The term fluorescence relates to phenomena in which the time interval between absorption and emission of energy is extremely short, typically in the range of 0.01–1000 microseconds. The term "phosphorescence" relates to the emission of radiation continuing after excitation has ceased, and may last from a fraction of a second to an hour or more.

The fluorescence of metallic conductors on PCBs, such as copper, under short wavelength visible light (for example 442 nm laser light emitted by a helium cadmium CW laser) is measurably less, generally by an order of magnitude, than the fluorescence of typical PCB laminate materials, such as glass-epoxy or polyamide. In addition, copper reflects light much better than such typical PCB laminate materials. The present invention exploits the large differences in fluorescence and reflectance of laminate compared to conductor in order to distinguish between portions of the via which are laminate and portions which are copper.

The reflectance and luminescence sensors preferably are placed above a horizontal PCB to be inspected, and are angled with respect to the via. The angled orientation of the sensors permits them to view and to provide sensed information along the entire depth of the via. By simultaneously combining and analyzing sensor inputs from at least two channels, the AOI system can detect and distinguish between at some of the various defects shown in FIGS. 1A–1F. The combined information can distinguish between defects in the via as opposed to defects on the upper surface of the PCB or at the bottom of the via. Most importantly, the combined information can distinguish between underdrilling or residue debris which can be repaired by further laser drilling, and other defects such as via hole misalignment that generally can not be readily repaired. Preferably the sensor inputs are signals from the combination of two of the luminescent, reflective and transmissive sensors respectively. Alternatively, the sensor inputs may be two signal inputs from the luminescent sensor, or two inputs from the reflective sensor, wherein each input is interpreted with reference to one of various thresholds of luminescence or reflectance, and then combined to detect the presence of defects.

The transmission sensor, simultaneously with the reflectance and luminescence sensors, can sense light that passes through the hole from one side of the PCB to another, thereby providing information regarding the position, and possible defects, of through holes. The sensitivity of the system can be adjusted as desired, in order to distinguish between defects which are sufficiently small in size so as not to pose any problem in plating or electrical conductivity, as opposed to those defects which are of a size sufficient to pose a problem. For example, by adjusting the sensitivity of the system, the system can distinguish between debris remaining in a via which may hinder plating or electrical conductivity, for example debris which is 3–4 $\mu$m size, as opposed to debris which is not considered a hindrance to plating or electrical conductivity, for example debris of only 1 $\mu$m size.

The system can also be used to scan a PCB before or after cleaning the PCB with a cleaning agent, or before or after plating. Preferably, when the system is used to inspect a PCB prior to cleaning, only one input is used, for example from the luminescence sensor, however the signal from the one sensor is analyzed with respect to two different thresholds and then combined to determine the presence of defects.

Additionally, the system can be used to inspect substantially all the vias on a region of a PCB and automatically distinguish between repairable and not repairable vias in the inspected region. Those vias which are deemed repairable are subsequently repaired. Preferably, repairable and not repairable vias are distinguished as a function of one or more of the type of defect and the location of the defective via. Thus, for example, underdrilled vias may be deemed repairable and thus may be subsequently automatically further drilled so that adequate electrical contact can be made with the affected via. Preferably, the system includes an intelligent decision tree so that if a PCB includes a non-repairable via, for example an overdrilled or misaligned via, none of the repairable vias on the PCB are automatically repaired in order to conserve repair resources.

There is thus provided in accordance with a preferred embodiment of the present invention an automated optical inspection system including an automated optical inspection system including a source of electromagnetic radiation for delivering a radiation beam on an article to be inspected;

a plurality of sensors arranged with respect to the radiation beam for sensing a plurality of radiation properties associated with the radiation beam impinging at least at a zone of impingement on a substance found on the article to be inspected, wherein the plurality of sensors includes a luminescence sensor for sensing luminescence of the substance due to the beam impinging thereon and a reflectance sensor for sensing reflectance of the beam from the substance and wherein the sensors transmit information signals based on the radiation properties sensed by said sensors; and a processor in communication with said sensors operative to receive the information signals for a plurality of zones of impingement, to combine said signals from the sensors and to analyze them, and to generate an output indicating the presence of defects based on said analysis.

Preferably, a preferred embodiment of the system includes at least one or more of the following:

The defects include defects that are automatically repairable and defects that are not automatically repairable.

The luminescence sensor is a fluorescence sensor.

The article to be inspected is PCB with a via formed which has a depth, and the reflectance and luminescence sensors are positioned at an angle with respect to the via, such that said sensors can view and provide sensed information generally along the entire depth of said via.

The sensors have an adjustable sensitivity.

The sensitivity of each sensor is adjustable independently of the other.

The position of each sensor is adjustable independently of the other.

The radiation beam is a laser beam.

The processor comprises a filter to filter out a level of luminescence which could cause a false alarm.

The processor includes a filter to filter out a level of reflectance which could cause a false alarm.

The processor processes the information signals into binary signals with reference to predetermined detection thresholds for luminescence and reflectance.

The processor generates a binary image for each of luminescence and reflectance signals.

The processor multiplies the binary images together, and calculates a composite luminescence and reflectance image.

The processor compares the composite images to predetermined defect parameters, and produces a defect report.

The system includes a drilling laser unit operative to drill a hole or via in a PCB; the automated optical inspection system and said drilling laser are in electrical communication with a controller; and a position of the hole or via is fed from the automated optical inspection system to the controller, and the controller instructs the drilling laser to drill the hole or via.

The position of the hole or via is fed from the automated optical inspection unit if said hole or via is analyzed by the processor to be defective and repairable.

The drilling laser is operative to avoid drilling any holes or vias on said PCB if any said hole or via is determined by the automated optical inspection system to be defective and not repairable.

The drilling laser comprises a $CO_2$ laser.

The controller is also the processor.

The drilling laser is said source of electromagnetic radiation for delivering a radiation beam on an article to be inspected.

There is thus provided in accordance with a preferred embodiment of the present invention an automated optical inspection system including:

a source of electromagnetic radiation for delivering a radiation beam onto an article to be inspected;

a sensor arranged with respect to the radiation beam for sensing a radiation property associated with said radiation beam impinging at least at a zone of impingement on a substance found on the article to be inspected, wherein the sensor transmits information signals based on the radiation properties sensed by said sensor; and a processor in communication with said sensor, the processor being operative to:

receive information signals for a plurality of zones of impingement, extract from the information signal additional information about said article by analysis of the information signals with reference to at least two different thresholds; and generate an output indicating the presence of a defects based on analysis of the extracted information.

Preferred embodiments of the invention include one or more of the following:

The processor further includes an information combiner operative to combine additional information about said article obtained by analysis of the information signals with reference to the at least two different thresholds.

The detected defects include defects that are classified as automatically repairable and defects that classified as being not automatically repairable.

The sensor is a luminescence sensor operative to sense fluorescence.

The article to be inspected is a PCB with a via formed therein, wherein the via has a depth, and wherein the luminescence sensor is positioned at an angle with respect to the via, such that it can view and provide sensed luminescence information generally along the entire depth of said via.

The sensor has an adjustable sensitivity.

The radiation beam is a laser beam.

The processor includes a filter to filter out a level of luminescence which could cause a false alarm.

The processor processes the information signals to produce a set of binary images with reference to at least two different predetermined detection thresholds for luminescence.

The processor multiplies the binary images together, and calculates therefrom a composite image.

The processor compares the composite image to predetermined defect parameters, and produces a defect report based on the comparison.

The system further includes a drilling laser operative to drill a hole or via in a PCB; automated optical inspection system and the drilling laser are in electrical communication with a controller, and a position of the hole or via is fed from said automated optical inspection system to the controller, which instructs said drilling laser to drill the hole or via.

The position of the hole or via is fed from said automated optical inspection device if said hole or via is analyzed by the processor to be defective and repairable.

The drilling laser is operative to avoid drilling holes or vias on said PCB if upon inspection a hole or via on the PCB is determined by the automated optical inspection system to be defective and not repairable.

The laser comprises a $CO_2$ laser.

The controller is said processor.

The drilling laser is the source of electromagnetic radiation for delivering a radiation beam on an article to be inspected.

There is thus provided in accordance with a preferred embodiment of the present invention, a system for repairing defective laser drilled holes in an electrical circuit to be inspected including:

an automated optical inspection subsystem operative to inspect a PCB and to provide output indications of defective and non-defective vias on the PCB, and a controller in communication with the automated optical inspection system and with a laser drill, wherein the controller is operative to instruct the laser drill to automatically redrill at least some holes on the PCB indicated as being defective.

The output indication of repairable and non-repairable holes further indicates which defective holes are repairable, and the laser drill automatically redrills defective and repairable holes.

The laser drill avoids drilling any holes if the automated optical inspection system detects a defective and non-repairable hole.

The laser drill is a $CO_2$ laser drill.

The laser is a YAG laser drill, and the automated optical inspection system determines a characteristic of repairable defective holes.

The characteristic of a repairable defective hole is the size of an artifact in the hole.

The characteristic of a repairable defective hole is the thickness of a residue laminate in the hole.

The laser drill is operative to provide an amount of energy adapted to clear the hole without overdrilling the hole.

BRIEF DESCRIPTION OF THE DRAWINGS

The present invention will be understood and appreciated more fully from the following detailed description, taken in conjunction with the drawings in which:

FIG. 4A is simplified sectional illustration of a defectless via;

FIG. 4B is a simplified illustration of graphs of fluorescence and reflectance associated with the via of FIG. 4A;

FIG. 4C is a simplified illustration of binary images corresponding to the fluorescence and reflectance associated with the via of FIG. 4A, and a combined image of the binary images;

FIG. 5A is simplified sectional illustration of a via with an artifact;

FIG. 5B is a simplified illustration of graphs of fluorescence and reflectance associated with the via of FIG. 5A;

FIG. 5C is a simplified illustration of binary images corresponding to the fluorescence and reflectance associated with the via of FIG. 5A, and a combined image of the binary images;

FIG. 6A is simplified sectional illustration of a via with first underdrilled hole;

FIG. 6B is a simplified illustration of graphs of fluorescence and reflectance associated with the via of FIG. 6A;

FIG. 6C is a simplified illustration of binary images corresponding to the fluorescence and reflectance associated with the via of FIG. 6A, and a combined image of the binary images;

FIG. 7A is simplified sectional illustration of a via with a second underdrilled hole, shallower than the underdrilled hole of FIG. 6A;

FIG. 7B is a simplified illustration of graphs of fluorescence and reflectance associated with the via of FIG. 7A;

FIG. 7C is a simplified illustration of binary images corresponding to the fluorescence and reflectance associated with the via of FIG. 7A, and a combined image of the binary images;

FIG. 8A is simplified sectional illustration of a via with an overdrilled hole;

FIG. 8B is a simplified illustration of graphs of fluorescence and reflectance associated with the via of FIG. 8A;

FIG. 8C is a simplified illustration of binary images corresponding to the fluorescence and reflectance associated with the via of FIG. 5A, and a combined image of the binary images;

FIG. 9A is simplified sectional illustration of a misregistered via;

FIG. 9B is a simplified illustration of graphs of fluorescence and reflectance associated with the via of FIG. 9A;

FIG. 9C is a simplified illustration of binary images corresponding to the fluorescence and reflectance associated with the via of FIG. 9A, and a combined image of the binary images;

DETAILED DESCRIPTION OF A PREFERRED EMBODIMENT

Figure 1A:
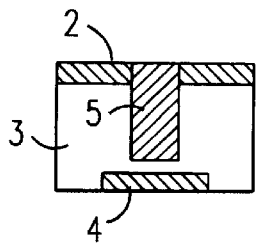
FIGS. 1A–1F are six simplified sectional illustrations of different defects associated with laser-drilled vias of the prior art.
Figure 1B:
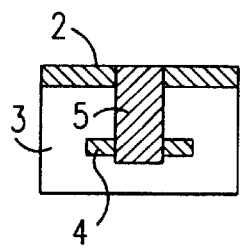
Figure 1C:
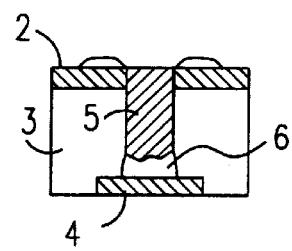
Figure 1D:
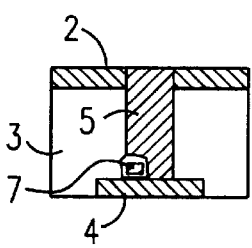
Figure 1E:
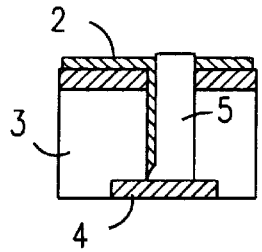
Figure 1F:
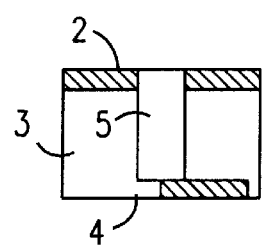
Figure 2:
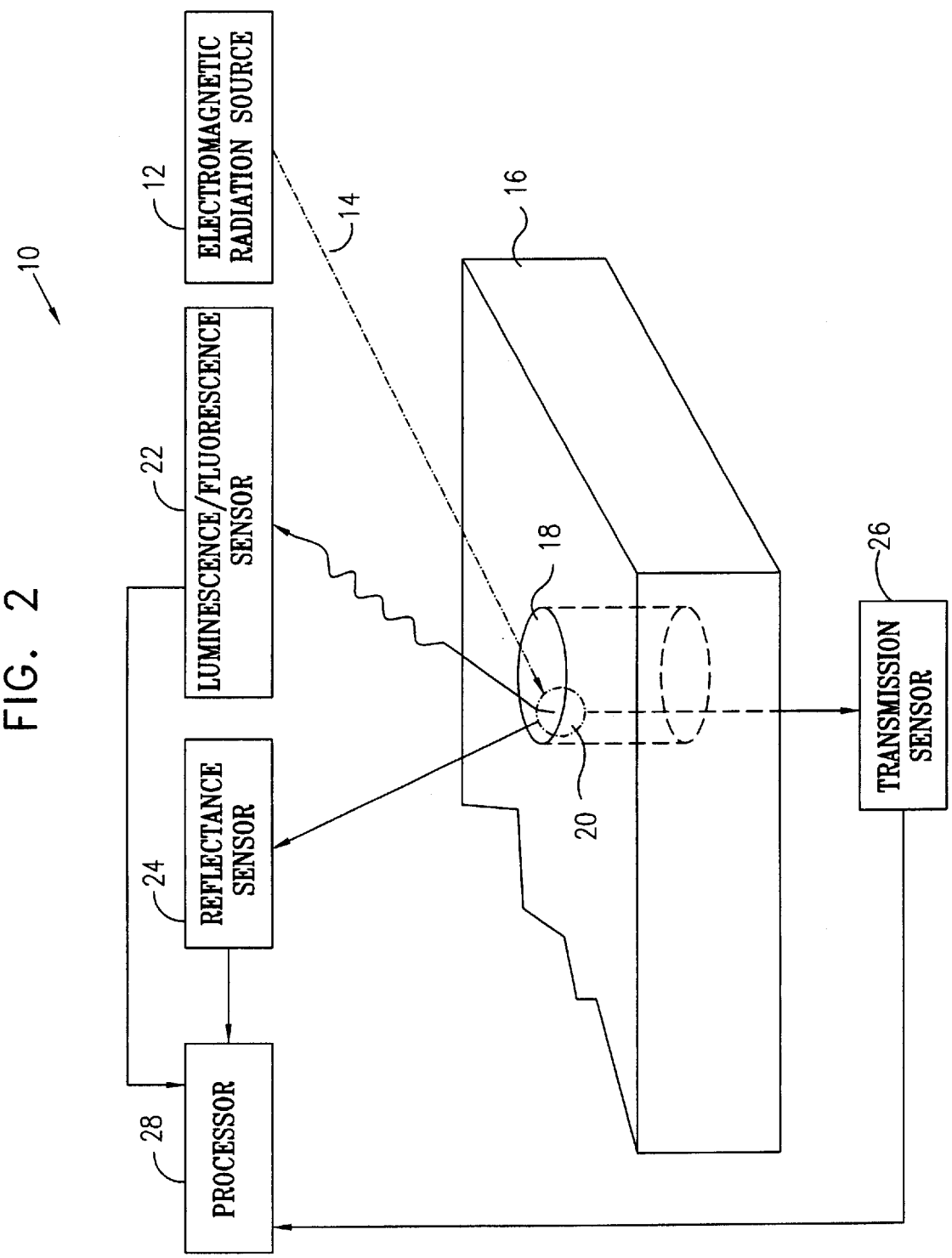
FIG. 2 is a simplified block diagram illustration of an automated optical inspection system constructed and operative in accordance with a preferred embodiment of the present invention.

Reference is now made to FIG. 2 which illustrates an automated optical inspection system 10 constructed and operative in accordance with a preferred embodiment of the present invention.

System 10 preferably includes a source 12 of electromagnetic radiation for delivering a radiation beam 14 to an article to be inspected. A preferred radiation source is a laser, such as a 10 mW helium-cadmium CW laser available from Liconix of California, U.S.A., but it is appreciated that the present invention encompasses any kind of suitable laser or radiation source. A typical article to be inspected is a suitable electrical circuit, such as a PCB 16 with a via 18 formed therein. Via 18 may be a via having any arbitrary depth to reach some predetermined inner layer in a multi-layered PCB 16, or a through hole passing all the way through PCB 16. Via 18 may be formed by mechanical drilling, by drilling using a suitable laser drill such as a $CO_2$, YAG or eximer laser, by etching or by any other suitable via hole generation process.

A plurality of sensors are preferably arranged with respect to radiation beam 14 for sensing a plurality of radiation properties associated with radiation beam 14 impinging at a zone of impingement 20 (shown as a phantom-line circle in FIG. 2) on a substance found on the article to be inspected. The "substance" can be the wall of the via 18, an artifact found in the via, a defect in the via, extraneous matter, solvents, etc. The plurality of sensors preferably includes a luminescence sensor 22 for sensing luminescence, such as fluorescence or phosphorescence, of the substance due to beam 14 impinging thereon, a reflectance sensor 24 for sensing reflectance of beam 14 from the substance, and a transmission sensor 26 for sensing transmission of beam 14 at the zone of impingement 20. The sensors 22, 24 and 26 transmit information signals based on the radiation properties sensed by sensors 22, 24 and 26 to a processor 28 that processes the signals for each zone of impingement of beam 14. A scanner (not shown) may be used to pass beam 14 over the entire area and depth of via 18, for example in a sequence of swaths or other suitable systematic pattern.

Each sensor 22, 24 and 26 preferably has an adjustable sensitivity, and the position and/or sensitivity and/or threshold of detectivity of each sensor can be adjusted independently of the other. In this manner, the performance of system 10 can be adjusted and optimized as required. Additionally, as will be described in greater detail hereinbelow, a signal from either luminescence sensor 22 or reflectance sensor 24 respectively may be simultaneously processed with reference to separate thresholds to extract additional information from the signal, and subsequently the additional information is combined in order to detect various different defects that would not be detectable by using a single signal from any one of luminescence sensor 22, reflectance sensor 24 and transmission sensor 26, or by combining any plurality of signals from one or more of the sensors 22, 24 and 26. Reflectance and luminescence sensors 22 and 24 are preferably positioned at an angle with respect to via 18, such that sensors 22 and 24 can view and provide sensed information generally along the entire depth of via 18.

A preferred luminescence sensor 22 is a photo sensor, preferably a photo diode or photomultiplier type sensor operative to sense fluorescence/phosphorescent emission, although other types of sensors may be employed depending upon the article being inspected and the energy level and/or quantity of radiation to be sensed.

Figure 3:
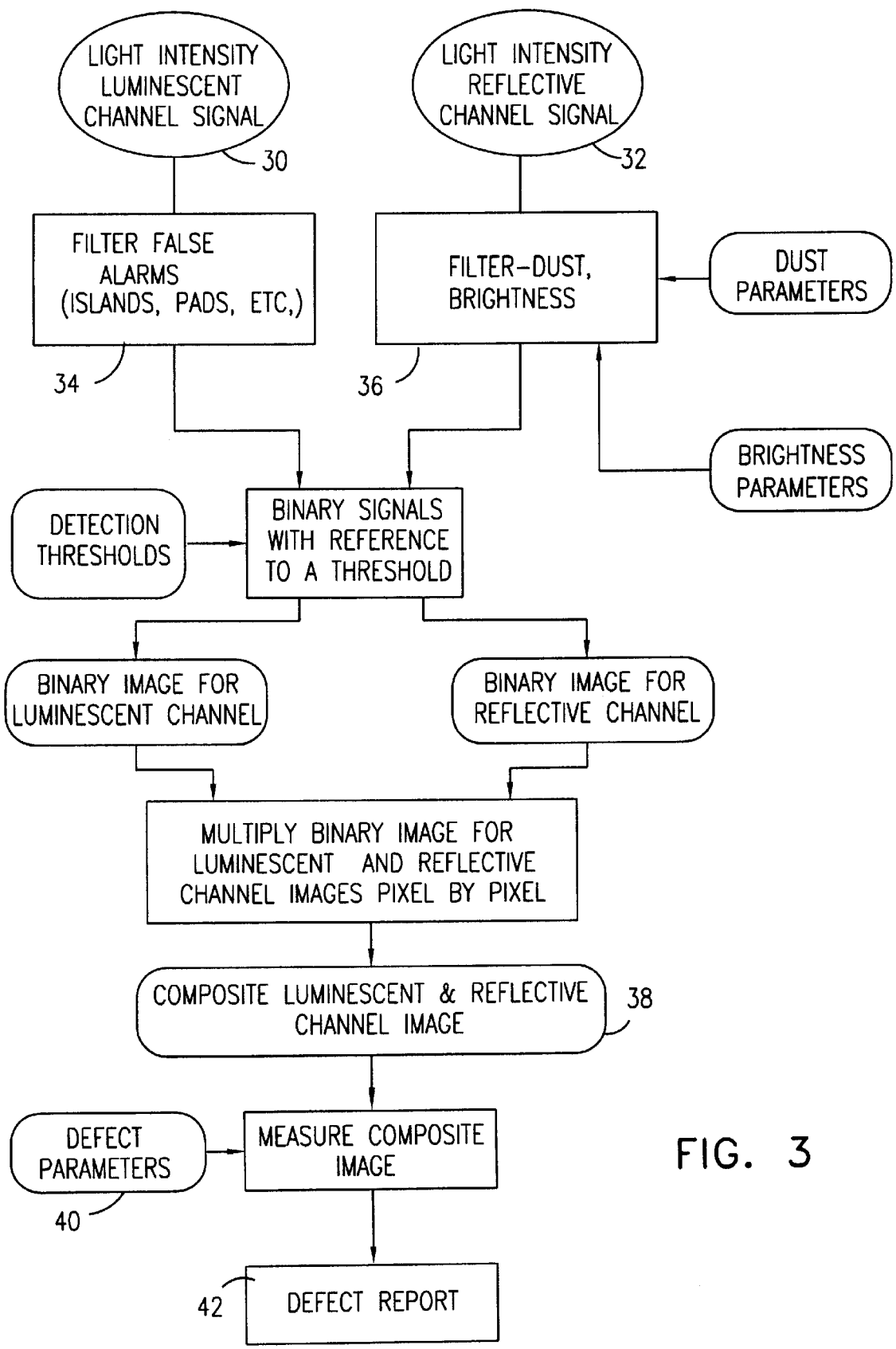
FIG. 3 is a simplified flow chart of the system of FIG. 2.

Reference is now made to FIG. 3 which is a simplified flow chart of system 10 illustrating operation thereof in accordance with a preferred embodiment of the present invention. Luminescence sensor 22 provides information related to the luminescent intensity of light emissions resulting from beam 14 impinging on zone 20 and this information is fed to a luminescent intensity channel 30 of processor 28. Similarly, reflectance sensor 24 provides information related to the reflective intensity of light from beam 14 being reflected from zone 20 and this information is fed to a reflective intensity channel 32 of processor 28.

Luminescent intensity channel 30 preferably is provided with one or more filters 34 that filter out spurious appearances of luminescence typically associated with false alarm defects, such as islands, pads, etc. Similarly, reflective intensity channel 32 is preferably provided with one or more filters 36 that filter out spurious appearances of reflectance typically associated with false alarm defects, such as those associated with brightness or tolerable sizes of particles, such as dust, for example. Filters 34 and 36 may be optical filters or a processor (not shown) applying suitable algorithms, for example. Appropriate filtering parameters and sensitivity may be pre-set, manually adjustable or programmable, as desired.

The outputs of channels 30 and 32 as filtered by filters 34 and 36, respectively, are processed by processor 28 into binary signals with reference to predetermined detection thresholds for luminescence and reflectance respectively. A binary image is generated for each channel 30 and 32, and these binary images are combined, preferably by multiplying them together, pixel by pixel. In this manner, processor 28 calculates a composite luminescence and reflectance channel image 38.

The composite image 38 is then measured and analyzed with reference to a predetermined defect parameters 40. For example, typical defect parameters include a net pad size or a particle size threshold. A typical particle size threshold would be a particle size of 1 µm, because such a size is not considered a hindrance to plating or electrical conductivity. Based on these defect parameters 40 and the composite images 38, a defect report 42 is produced, which may be displayed or printed, for example.

Reference is now made to FIGS. 4A, 4B and 4C which pictorially illustrate how the luminescence and reflectance signals are combined, as described hereinabove with reference to FIG. 3, to detect defects. FIG. 4A illustrates a defectless via 50 with an upper copper layer 52 and a lower copper pad 54, separated by a laminate 56. Beam 14 (FIG. 2) scans the entire depth and area of via 50. For each scan pass of beam 14 over a via 50, as seen in FIG. 4B, a luminescence intensity in the example shown, relating to fluorescence and designated graph F, and a reflectance intensity, designated graph R, are sensed. It is noted that a via 50 preferably is sensed in multiple passes of scan beam 14. Additionally it is seen in graph F that for a fluorescence sensor, the fluorescence of the copper layer 52 and pad 54 is relatively low, whereas the fluorescence of the laminate 56 forming walls 57 of via 50 is relatively high. Thus the fluorescence of laminate 56 appears as two peaks in the fluorescence graph F of FIG. 4B. The peaks are above a predetermined fluorescence threshold FT, which means that processor 28 recognizes them as peaks associated with a non-metal material.

Conversely, as seen in graph R of FIG. 4B the reflectance of the copper layer 52 is relatively high, whereas the reflectance of the laminate 56 is relatively low. Typically, the reflectance of copper layer 52 is higher than the reflectance of pad 54 because pad 54 is more distant from reflectance sensor 24 (FIG. 2). Preferably a predetermined reflectance threshold RT is set intermediate of typical reflectance levels of copper layer 52 and pad 54 so as to define the circumference boundary of via 50. Thus the reflectance of laminate 56 appears as two reverse peaks in the reflectance graph R of FIG. 4B. Inasmuch as reflectance of the copper layer 52 is above threshold RT, while the reflectances of pad 54 and laminate 56 are below that threshold, processor 28 can readily distinguish between them to spatially define the circumference of via 50.

In FIG. 4C, it is seen that a binary image of all of subsequent scanning passes of the fluorescence sensor is generated. The binary image is taken with respect to thresholds FT and RT and includes a central, shaded circular region 58 inside a clear, circular ring 60, which is in turn bounded by a shaded region 62. The clear ring 60 corresponds to the part of the signal represented in graph F and shown as fluorescence peaks associated with the laminate walls of the via 50 which are above threshold FT, whereas regions 58 and 62 correspond to fluorescence signal in graph F for pad 54 and layer 52, respectively. Conversely, a binary image of all of the scanning passes of the reflectance sensor is generated. The binary image includes a circular region 64 corresponding to the reflectance of pad 54 and laminate 56, both of which are below reflectance threshold RT, which is bounded by a clear region 66 which corresponds to the reflectance of pad 52 and is above threshold RT. Thus, as seen, circular region 64 defines the spatial region of via 50.

In accordance with a preferred embodiment of the present invention, each of the shaded regions 58, 62 and 64 shown in FIG. 4C are assigned a value of 1, while each of the clear regions 60 and 66 are assigned a value of 0. Processor 28 multiplies these values together to form a composite image 70, shown in FIG. 4C, which indicates the spatial region inside via 50 which are suitable for electrical contact. Thus composite image 70, shown in FIG. 4C, is seen to represent a defectless via 50 in which the entire spatial region inside via 50 is suitable for electrical contact.

Reference is now made to FIGS. 5A, 5B and 5C which pictorially illustrate how the luminescence and reflectance signals are combined to detect a defect due to the presence of an artifact that partially covers pad 54. FIG. 5A illustrates via 50 with an artifact 72, such as debris left over from an etching process, on lower copper pad 54. The fluorescence of laminate 56 forming walls 57 still appears as two principal peaks in the fluorescence graph F of FIG. 5B, but there is an additional peak associated with artifact 72. As seen, some part of each of the peaks, including the peak associated with artifact 72, extends above a predetermined fluorescence threshold FT, which means that processor 28 recognizes these peaks as being associated with a non-metal material.

Conversely, as seen in graph R of FIG. 5B, the reflectance of the copper layer 52 is relatively high, whereas the reflectance of pad 54, laminate 56, artifact 72 each are below the reflectance threshold RT. Note that the reflectance of artifact 72 is different than that of pad 54 and of laminate 56, however in the example shown each of the respective intensities of reflectance is less than reflectance threshold RT.

In FIG. 5C, it is seen that the binary images of the fluorescence and reflectance channels, taken with respect to thresholds FT and RT, are combined in the manner described with respect to FIG. 4C hereinabove to form a composite image 74 corresponding to composite image 70 in FIG. 4C. It is seen that anomaly 76 corresponds to artifact 72 (FIG. 5A), namely a non-metal fluorescent body that is located in a region that should be completely occupied by copper pad 54. Depending on the size of anomaly, via 50 may be classified as defective or non-defective in accordance with inspection parameters.

Reference is now made to FIGS. 6A, 6B and 6C and to FIGS. 7A, 7B and 7C which pictorially illustrate how the luminescence and reflectance signals are combined to detect a defect due to an underdrilled hole, it being noted that sometimes a thin layer of residue laminate may not necessarily render a via defective, while conversely a thicker layer or residue laminate may result in a defect. FIGS. 6A, 6B and 6C illustrate a partially underdrilled hole which is not defective while FIGS. 7A, 7B and 7C illustrate an underdrilled hole having a thicker residue laminate that is defective.

FIG. 6A illustrates a first underdrilled via hole 78 having an underdrilled region 79 thereinside. Although via 78 is underdrilled it is not defective. As seen in FIG. 6B, the fluorescence intensity of laminate 56 received from the walls 57 still appears as two peaks in the fluorescence graph F, and the fluorescence of underdrilled hole 78 is seen to be different than that of via 50 as shown in FIG. 4B. It is noted that the fluorescence intensity between the peaks in graph F of FIG. 6B, corresponding to underdrilled region 79 is higher than graph F of FIG. 4B. This is because in underdrilled via hole 78 a thin layer of residue due to underdrilling is present in underdrilled region 79 which typically results in a small but measurable luminescent intensity. Furthermore, it is seen that despite the presence of luminescence, the intensity of graph F of FIG. 6B does not exceed fluorescence intensity threshold FT, thus indicating that pad 54 in FIG. 6A laminate residue 79 is not so thick as to prevent good electrical contact with pad 54.

Conversely, the reflectance of copper layer 52 in FIG. 6A is relatively high, whereas the reflectance of laminate 56 forming walls 57 and pad 54 in underdrilled via hole 78 are relatively low. Note that although the reflectance graph R of underdrilled via hole 78 is different than reflectance graph R of defectless via 50 (FIG. 4A), the reflectance graph R corresponding to pad 54 of underdrilled hole 78 likewise does not exceed threshold RT in FIG. 6B.

In FIG. 6C, it is seen that binary images of the fluorescence and reflectance channels, taken with respect to thresholds FT and RT, are combined to form a composite image 80 which is substantially similar to composite image 70 for defectless via 50. It is noted that although a residue is present, suitable electrical contact with a pad 54 may still be made. Thus because the luminescence is below threshold FT no defect is detected.

Reference is now made to FIGS. 7A, 7B and 7C which pictorially illustrate how the luminescence and reflectance signals are combined to detect a defect due to another underdrilled hole which has a quantity of residue that renders the underdrilled hole defective. FIG. 7A illustrates an underdrilled via hole 84, underdrilled via hole 84 being shallower, namely it contains a greater quantity of residue in underdrilled region 85, as compared to underdrilled via hole 78 of FIG. 6A. As seen in graph F of FIG. 7B the fluorescence of laminate 56 forming walls 57 still appears as two peaks, but the fluorescence of the region 85 inside underdrilled via hole 84 is seen to be different than that of defectless via 50, as shown in FIG. 4B, and different than that of underdrilled hole 78, as shown in FIG. 6B. It is noted that the fluorescence intensity between the peaks in graph F of FIG. 7B is higher than graph F of FIG. 4B and graph F of FIG. 6B. This is because in underdrilled via hole 84 a relatively thick layer of residue is present in underdrilled region 85, which typically results in a relatively large measurable luminescent intensity. Furthermore, it is seen that the luminescent intensity graph F of FIG. 7B exceeds fluorescence intensity threshold FT, thus indicating a defect because suitable electrical contact can not be made with pad 54 in FIG. 7A.

In FIG. 7C, it is seen that binary images of the fluorescence and reflectance channels, taken with respect to thresholds FT and RT, are combined to form a composite image 90. Because fluorescent graph F in FIG. 7B exceeds threshold FT, it is seen in FIG. 7C that there is only a clear region 92 and shaded region 58 (FIG. 4C) is absent. Thus upon multiplication with circular region 64 in FIG. 7C, which defines the spatial region of underdrilled via hole 84 received from graph R, a null result is obtained, as shown by the phantom lines of composite image 90 which indicate where the pad should have been located. Thus it is indicated that pad 54 is entirely covered and suitable electrical contact therewith can not be made.

It is thus appreciated from FIGS. 6B, 6C and 7B and 7C that processor 28 (FIG. 2) can distinguish between different depths of underdrilled holes. Moreover, by choosing appropriate thresholds FT and RT, the sensitivity of a via to the presence of underdrilling residue may be determined. Thus for example, a first threshold may be applied to various vias that require a very high level of cleanliness, while another threshold may be applied to vias where a larger quantity of residue is still acceptable without rendering the via defective. Such thresholds may be applied for example as a function of physical location in an electrical circuit, or as a function of a type or intended use. Additionally, multiple thresholds (not shown) may be provided to the same via such that a first threshold is used to ascertain the presence of a residue while a second and additional thresholds may be provided to determining the quantity of residue in the via. Such a multiple threshold arrangement may be beneficial, for example, in deciding first whether or not to redrill or clean out an underdrilled via 78, and additionally to determine the amount of laser energy that needs to be applied to clean out the via, for example if a YAG laser is used, in order to ensure that redrilling does not damage the via by over drilling.

Reference is now made to FIGS. 8A, 8B and 8C which pictorially illustrate how the luminescence and reflectance signals are combined to detect a defect due to an overdrilled via hole. FIG. 8A illustrates an overdrilled via hole 100, i.e., a via hole having a break 102 in pad 54. As seen in FIG. 8B, the fluorescence intensity of laminate 56 in walls 57 of overdrilled via hole 100 still appears as two peaks in the fluorescence graph F, however fluorescence graph F of overdrilled hole 100 also includes a spike 104 representative of break 102 intermediate of the peaks representing laminate 56.

Conversely, as seen in graph R of FIG. 8B, the reflectance of copper layer 52 is above the reflectance threshold RT while the reflectance of sections of pad 54 surrounding break 102, although relatively high, are less than reflectance threshold RT. The reflectance of laminate 56 forming walls 57 and laminate 56 underneath break 102 are also relatively low and less than the reflectance threshold RT. In FIG. 8C, it is seen that the binary images of the fluorescence and reflectance channels, taken with respect to thresholds FT and RT, are combined as described with respect to FIG. 4C to form a composite image 106 which has an anomaly 108 corresponding to break 102 in overdrilled hole 100.

It is noted that the composite image 106 of FIG. 8C representing an overdrilled hole is very similar to image 74 (FIG. 5C) showing an anomaly 76 that corresponds to an artifact 72 (FIG. 5A). In accordance with a preferred embodiment of the invention the distinction between a residue artifact and an overdrilled hole is made respective of the type of drilling process used to prepare the laser via. Thus for example, if the laser via was initially drilled using a $CO_2$ laser, which does not drill through copper, the anomaly is assumed to be an artifact 76. However, if the laser via was drilled using a YAG laser, which is able to drill through copper, the anomaly is assumed to be an overdrilled hole.

Reference is now made to FIGS. 9A, 9B and 9C which pictorially illustrate how the luminescence and reflectance signals are combined to detect a defect due to a misregistered hole. FIG. 9A illustrates via hole 110 misaligned with pad 54.

As seen in graph F of FIG. 9B, the fluorescence of laminate 56 appears as one peak associated with the right-hand laminate wall 112 that extends down to pad 54, and a broad band of relatively high fluorescence associated with the left hand wall 114 and a pad-less area of laminate 56 at the bottom of via hole 110.

Conversely, as seen in graph R of FIG. 9B the reflectance of copper layer 52 and is relatively high and is above threshold RT. The reflectance of laminate 56 appears as one reverse peak associated with the laminate wall 112 that goes down to pad 54, and a broad band of relatively low reflectance associated with the wall 114 and pad-less area of laminate at the bottom of via 50. The reflectance of pad 54 is relatively high compared to the reflectance of laminate 56, however it remains below threshold RT. In FIG. 9C, it is seen that the binary images of the fluorescence and reflectance channels, taken with respect to thresholds FT and RT, are combined to form a composite image 116 which due to misregistration between via hole 110 and pad 54 is misshaped, not round in the example shown, and small compared to a properly formed via hole, for example via 50 in FIGS. 4A–4C.

While the above discussion has been with respect to a binary composition of signals from the input channels, it is appreciated by persons skilled in the art that in order to further distinguish between different forms of defects various multiple thresholds or robust algorithms operative to analyze the analogue signal may be provided.

The present invention can be used to scan a PCB both before and after cleaning the PCB with a liquid cleaning solution. FIGS. 4A–9C illustrate inspecting the via 50 generally after cleaning the PCB with a liquid cleaning solution. The cleaning solution removes most of the debris left in the via and prepares the surface of copper layer 52 to be free of smudges and other artifacts that may affect reflectance or fluorescence. Typically when the PCB is cleaned before inspection there is a pronounced difference between the fluorescence of the copper pad 54 at the bottom of the via 50 and that of the laminate 56 which makes up the walls 57 of the via 50. There is also a large difference in the respective reflectances of copper layers 52 and pads 54 located at the bottom of the various vias.

Figure 10:
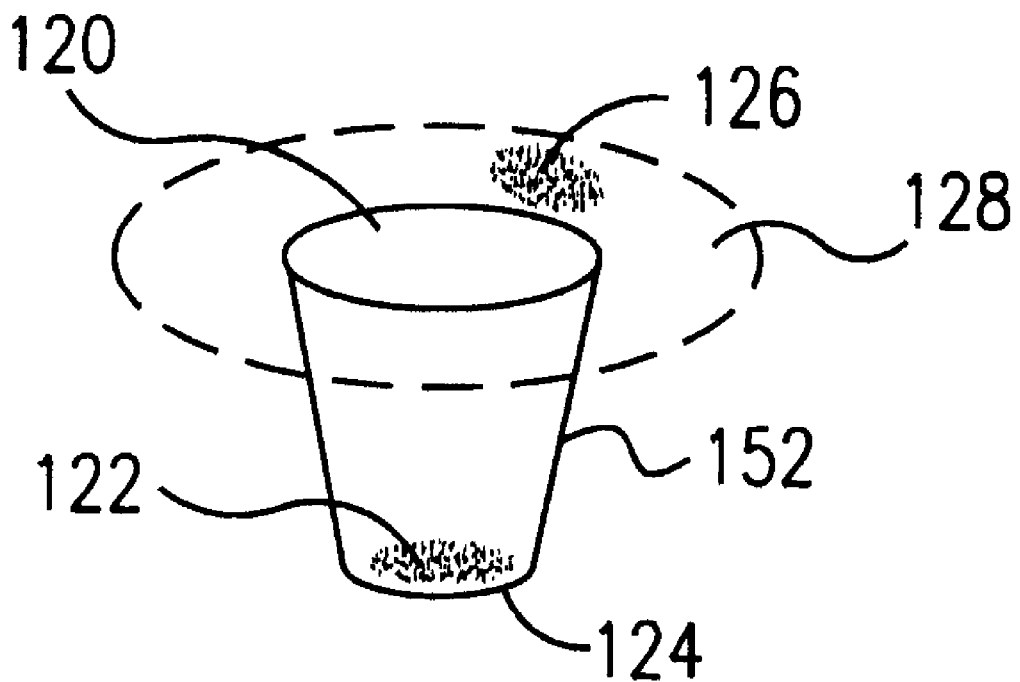
FIG. 10 is a simplified illustration of a via on a PCB before cleaning the PCB with a cleaning solution.
Figure 11:
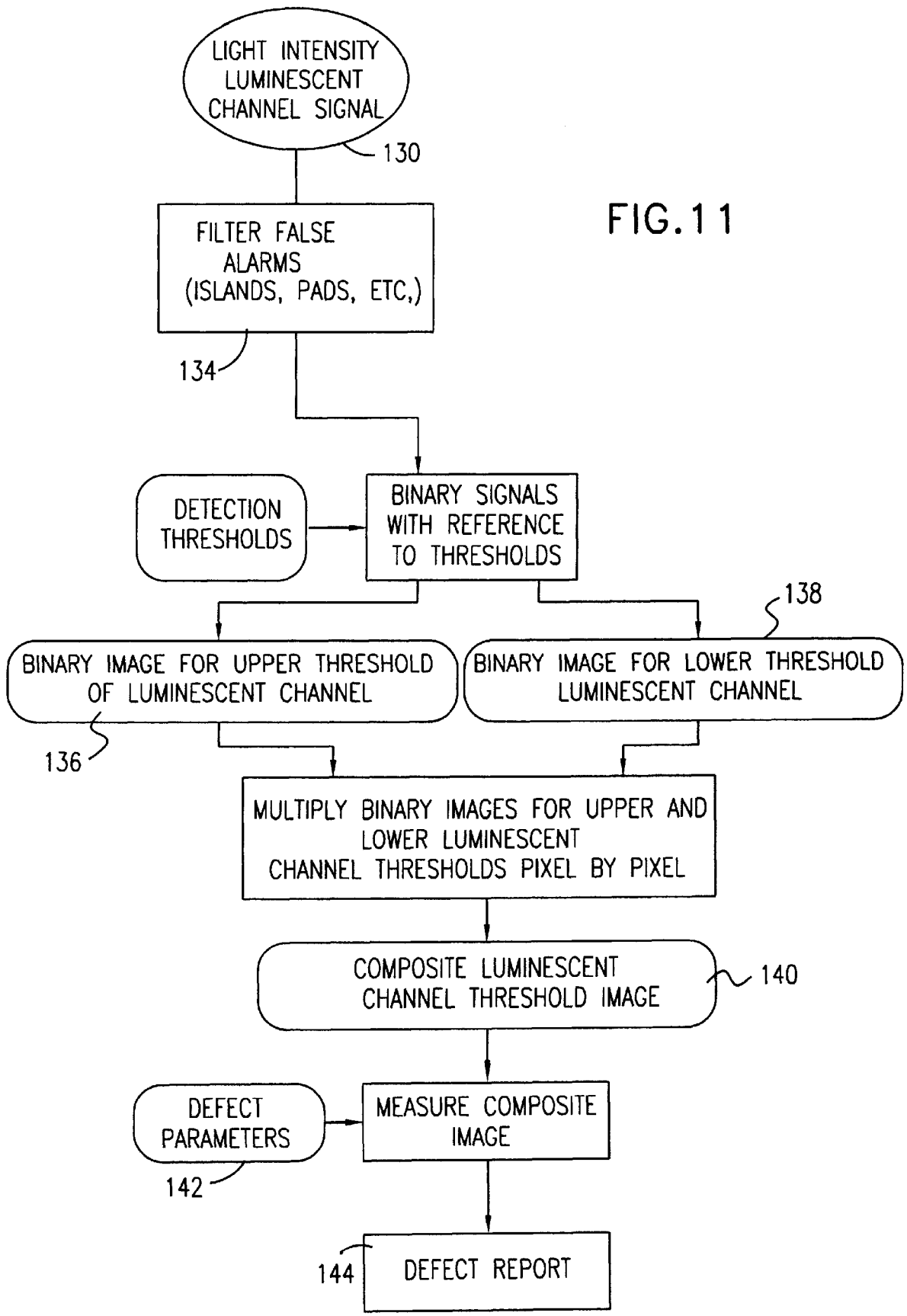
FIG. 11 is a simplified flow chart showing another preferred mode of operation of the system of FIG. 2.

Reference is now made to FIG. 10 which is a simplified illustration of a via on a PCB prior to cleaning the PCB with a cleaning solution, and to FIG. 11 which is a simplified flow chart showing another preferred mode of operation of the system of FIG. 2 in which a PCB is inspected prior to cleaning.

Referring to FIG. 10, it is seen that before cleaning the PCB with a cleaning solution, there may be at least some debris in a via 120 and its surroundings. Specifically, there is typically a thin laminate layer 122 at least partially covering a bottom pad 124 of via 120, and/or laminate material 126 or other non reflective debris may be deposited on an upper copper layer 128 near via 120, such as material thrown out during photoablation, fingerprint residue, oxidation and the like. Such debris generally reduces reflectance of the copper. Additionally, if the reflectance threshold is reduced to accommodate the reduced reflectance undesired shiny spots may appear on bottom pad 124, for example where thin laminate layer 122 does not cover the entire pad 124. It is thus appreciated that in such situations before cleaning, changes in the reflectance of the bottom pad 124 caused by thin laminate layer 122 and unevenness in reflectivity of the upper copper layer 128 may cause the reflective intensity channel 32 to provide irregular information or information that is significantly different from the information that would be provided after cleaning. These irregularities typically make it difficult to define the spatial boundaries of via 120 or to detect the presence of defects inside via 120.

In a preferred embodiment of the present invention, for inspection of PCBs before cleaning, the reflective intensity channel 32 is not used at all. Rather, the luminescent intensity signal for a non-defective via 120 is modeled and a signal (preferably fluorescence) from one of sensors 22 or 24 (FIG. 2) for each via 120 to be inspected preferably is analyzed with respect to two thresholds.

Referring now to FIG. 11, luminescence sensor 22 provides information related to the luminescent intensity of light emissions resulting from beam 14 impinging on zone 20 (FIG. 2) and this information is fed to a luminescent intensity channel 130 of processor 28.

Luminescent intensity channel signal 130 is preferably treated with one or more filters 134 that filter out spurious appearances of luminescence typically associated with false alarm defects, such as islands, pads, etc. Filter 134 may be an optical filters or suitable algorithm, for example. Appropriate filtering parameters and sensitivity may be pre-set, manually adjustable or programmable, as desired.

The outputs of channel signal 130 as filtered by filter 134 is processed by processor 28 into binary signals with reference to two predetermined detection thresholds, namely an upper threshold and a lower thereshold, as shown and described hereinbelow with respect to FIG. 12, to produce a first binary image respective of the upper threshold 136 and a second binary image respective the lower threshold 138. The first and second binary images for the upper and lower thresholds respectively are multiplied together, pixel by pixel, in the same manner as shown and described hereinabove, for example with reference to FIG. 4C. In this manner, processor 28 (FIG. 2) calculates a composite image 140.

The composite image 140 is then measured and compared to predetermined defect parameters 142. For example, one kind of defect parameter may be a minimum pad size or a particle size threshold. Based on these defect parameters 142 and the composite images 140, a defect report 144 is produced, which may be displayed or printed, for example.

Figure 12:
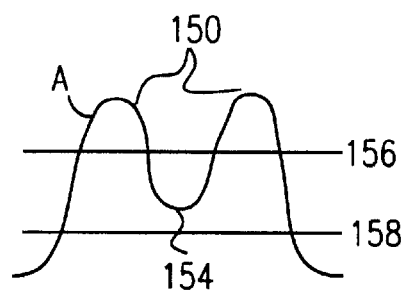
FIG. 12 is a simplified illustration of a graphs of fluorescence of the via shown with reference to a double threshold.

Reference is now made to FIG. 12 wherein graph A is a graph of fluorescence of a non-defective via 120 to be inspected before cleaning, wherein upper peaks 150 represent the fluorescent signal received from walls 152 of via 120 (FIG. 10), and lower valley 154 represents the fluorescent signal received from pad 124. It is noted that lower valley 154 has a small but measurable value due to the presence of a thin laminate layer 122 which has not been cleaned out of via 120.

By appropriately pre-setting a lower threshold 158 and an upper threshold 156, and ignoring the reflectance channel, processor 28 can apply lower threshold 158 to correctly identify the circumference boundary of via 120, similarly to reflective channel 32 (FIG. 3) and apply the upper threshold 156 to interpret whether the fluorescence value of the laminate layer 122 at the bottom of pad 124 is within an acceptable range for such a via before cleaning, or whether other defects, such as underdrilled laminate, breaks or unacceptably thick laminate are present.

Operation of the dual threshold is generally similar to and self-explanatory in view of FIGS. 4A–9C, wherein the values derived from graph A with reference to lower threshold 158 are used in place of values shown in graphs R in FIGS. 4B, 5B, 6B, 7B, 8B and 9B, obtained from light intensity reflective channel 32 with respect to threshold RT, in order to define the boundary of via 120. Thus, in the preferred embodiment used to inspect vias before cleaning, light intensity reflective channel signal 32 (FIG. 2) is replaced by a luminescence signal which is evaluated with respect to a low threshold 158. Light intensity luminescent channel 130 is analyzed with respect to upper threshold 156 to identify defects and its operation is substantially similar to operation of light intensity luminescent channel signal 30 as described in FIGS. 3A–9C.

The use of the information from luminescent intensity channel 130, and analysis with respect to two discreet thresholds, as opposed to analyzing information from both a luminescent intensity channel 30 and reflective intensity channel 32, has another benefit, in that system 10 becomes less sensitive or insensitive to bright spots at the bottom of via 120, which may result, for example, be an uneven coating or laminate residue covering pad 124.

It is appreciated that when applying a double threshold to luminescent intensity channel 130, typically it is necessary to model vias 120 and to filter the signal and adjust gain in order to ensure that a non-defective via produces a signal having distinguishable upper peaks 150 and intermediate lower valley 154 and to account for tolerances in the acceptable thickness of laminate residues 122 in the bottom of uncleaned via 120, namely residue thickness that do result in a defect. Preferably, lower threshold is situated at a level just below a minimum acceptable lower valley 154, and upper threshold can be situated at a level intermediate of lower valley 154 and upper peaks 150 depending on the desired sensitivity for detecting residue laminate or debris remaining inside via 120.

It is appreciated that an inspection system 10 may be equipped with circuitry to perform via inspection in accordance with either of the methods shown and described with reference to FIG. 3 and FIG. 11. Alternatively, inspection system 10 may be equipped with circuitry able to perform via inspection in accordance with both of the methods shown and described with reference to FIG. 3 and FIG. 11, in which case a switch is provided to enable a user to choose whether to inspect PCBs prior to or after cleaning.

Figure 13:
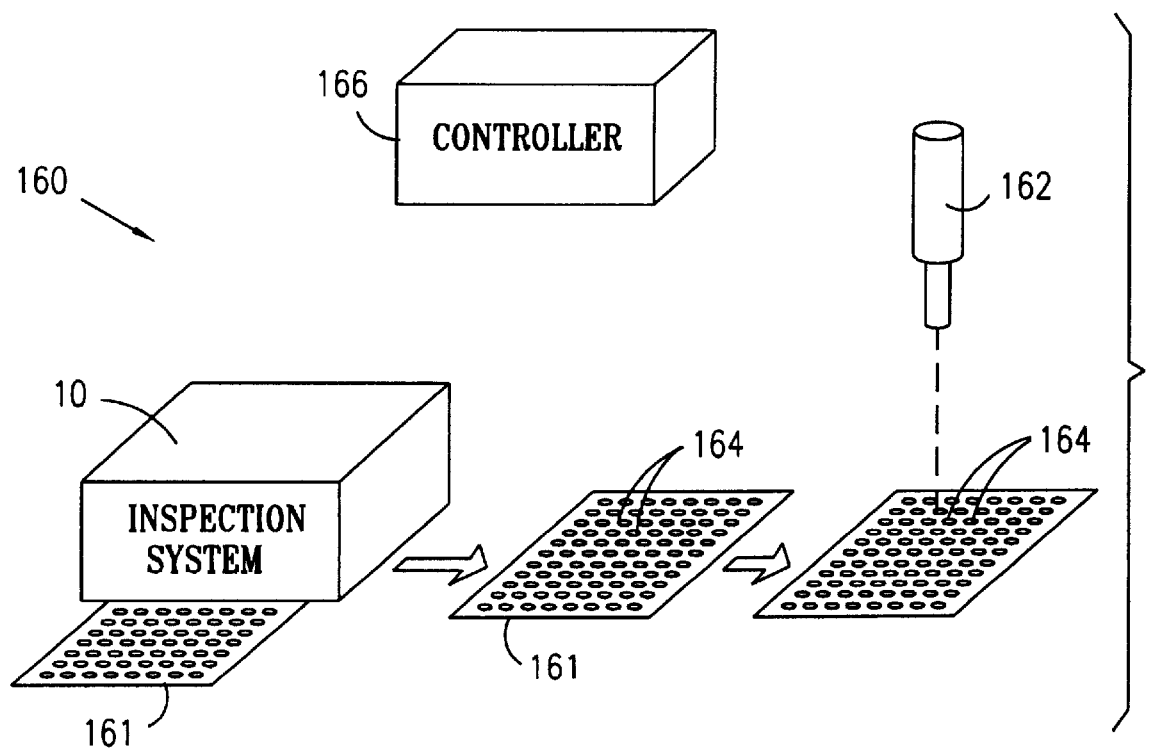
FIG. 13 is a simplified illustration of an automated optical inspection and PCB laser drilling system, constructed and operative in accordance with a preferred embodiment of the present invention.

Reference is now made to FIG. 13 which illustrates an automated optical inspection and PCB laser drilling system 160, constructed and operative in accordance with a preferred embodiment of the present invention. Automated optical inspection and PCB laser drilling system 160 preferably includes automated optical inspection system 10 which is used to inspect PCBs 161 as described hereinabove. In addition, system 160 includes a drilling laser 162 that drills holes or vias 164 in PCBs 161. Both system 10 and drilling laser 162 are in electrical communication with a controller 166. It is appreciated that drilling laser may be part of an integrated unit including inspection system 10 and controller 166, or may be an add-on or modular unit. Additionally, drilling laser may be operative to drill vias both before and after inspection, or alternatively drilling laser may be dedicated to the redrilling of vias only after inspection by inspection system 10.

Preferably system 10 is operative to automatically optically inspect the complete electrical circuit on a surface of a PCB 161, and to detect vias 164 which are either not defective, defective and repairable (for example underdrilled vias and vias having debris and residues therein) and non-repairable vias (for example vias having breaks or whose pads are misregistered). The position of defective and repairable vias 164 on PCB 161 is fed to controller 166, which instructs drilling laser 162 to redrill these vias 158, preferably automatically.

In accordance with a preferred embodiment of the invention, if a defective and not-repairable via is detected, for example a via with a break or a misregistered via, none of the vias 164 are redrilled, in order to conserve time and drilling resources. Thus if a defective and not repairable via is detected, the PCB 161 including such a defective and not repairable vias may be discarded or sent to a different, typically non automated, repair station at which the nature of the defect can be further evaluated and repaired as desired.

A preferred laser for redrilling the vias is a $CO_2$ laser, because such a laser will not drill into the lower metal layer, as mentioned hereinabove. Alternatively, inasmuch as manufacturing processes require, automated optical inspection and PCB laser drilling system 160 may incorporate a YAG or other laser that drills through both copper and laminate. When such a laser is used, a number of different thresholds are preferably applied in order to ascertain the existence of a defective via and to further determine the depth of under drilled laminates or residues remaining in via 120 (FIG. 10). Once the thickness of a residue is determined, laser driller is operative to automatically apply an appropriate quantity of laser energy to remove the underdrilled laminate or residue without destroying the pad 124 at the bottom of via 120. It is noted that controller 166 may be the processor 28 described hereinabove. It is further noted that it is possible to use the same laser to inspect and to drill the vias. Automated optical inspection and PCB laser drilling system 160 thus efficiently and rapidly inspects and drills vias or holes in PCBs.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An automated optical inspection system comprising:

a source of electromagnetic radiation for delivering a radiation beam on an electrical circuit to be inspected;

a plurality of sensors arranged with respect to said radiation beam for sensing a plurality of radiation properties associated with said radiation beam impinging at least at a zone of impingement on a substance found on the electrical circuit to be inspected, said plurality of sensors including a luminescence sensor for sensing luminescence of the substance due to the beam impinging thereon and a reflectance sensor for sensing reflectance of the beam from the substance said sensors transmitting information signals based on the radiation properties sensed by said sensors; and a processor in communication with said sensors operative to receive the information signals for a plurality of zones of impingement, to combine said signals from the sensors to generate a composite representation of said plurality of zones of impingement, said composite representation defining portions of said electrical circuit being detectable in a signal transmitted by a luminescence sensor and also being detectable in a signal transmitted by a reflectance sensor, to analyze said composite representation, and to generate an output indicating the presence of defects based on said analysis.

2. The system according to claim 1 and wherein said defects include defects that are automatically repairable and defects that are not automatically repairable.

3. The system according to claim 1 wherein said luminescence sensor comprises a fluorescence sensor.

4. The system according to claim 2 wherein said luminescence sensor comprises a fluorescence sensor.

5. The system according to claim 1 and wherein said electrical circuit includes a via formed therein, said via having a depth, wherein said reflectance and luminescence sensors are positioned at an angle with respect to the via, such that said sensors can view and provide sensed information generally along the entire depth of said via.

6. The system according to claim 1 wherein said sensors have an adjustable sensitivity.

7. The system according to claim 6 wherein the sensitivity of each sensor is adjustable independently of the other.

8. The system according to claim 1 wherein a position of each sensor is adjustable independently of the other.

9. The system according to claim 1 wherein said radiation beam comprises a laser beam.

10. The system according to claim 1 wherein said processor comprises a filter to filter out a level of luminescence which could cause a false alarm.

11. The system according to claim 1 wherein said processor comprises a filter to filter out a level of reflectance which could cause a false alarm.

12. The system according to claim 1 wherein said processor processes said information signals into binary signals with reference to predetermined detection thresholds for luminescence and reflectance.

13. The system according to claim 1 wherein said processor generates a binary image for each of luminescence and reflectance.

14. The system according to claim 13 wherein said processor multiplies said binary images together, and calculates a composite luminescence and reflectance image.

15. The system according to claim 14 wherein said processor compares said composite image to predetermined defect parameters, and produces a defect report.

16. The system according to claim 1 and further comprising a drilling laser operative to drill a hole or via in said electrical circuit, said automated optical inspection system and said drilling laser being in electrical communication with a controller, wherein a position of the hole or via is fed from said automated optical inspection system to said controller, which instructs said drilling laser to drill the hole or via.

17. The system according to claim 16 and wherein the position of the hole or via is fed from said automated optical inspection device if said hole or via is analyzed by the processor to be defective and repairable.

18. The system according to claim 16 and wherein said drilling laser is operative to avoid drilling any holes or vias on said electrical circuit if any said hole or via is determined by said automated optical inspection system to be defective and not repairable.

19. The system according to claim 16 wherein said drilling laser comprises a $CO_2$ laser.

20. The system according to claim 19 wherein said controller is said processor.

21. The system according to claim 16 wherein said controller is said processor.

22. The system according to claim 16 wherein said drilling laser is said source of electromagnetic radiation for delivering a radiation beam on an article to be inspected.

23. An automated optical inspection system comprising:
a source of electromagnetic radiation for delivering a radiation beam on an electrical circuit to be inspected;
a sensor arranged with respect to said radiation beam for sensing a radiation property associated with said radiation beam impinging at least at a zone of impingement on a substance found on the electrical circuit to be inspected, said sensor transmitting information signals based on the radiation properties sensed by said sensor; and
a processor in communication with said sensor and operative to:
receive the information signals for a plurality of zones of impingement,
extract from the information signal additional information about said electrical circuit by analysis of the information signals with reference to at least two different thresholds, and
generate an output indicating the presence of a defects based on analysis of the extracted information.

24. The system according to claim 23 and wherein the processor further comprises an information combiner operative to combine the additional information about said electrical circuit obtained by analysis of the information signals with reference to at least two different thresholds.

25. The system according to claim 24 and wherein said defects include defects that are classified as automatically repairable and defects that classified as not automatically repairable.

26. The system according to claim 23 and wherein said defects include defects that are classified as automatically repairable and defects that classified as not automatically repairable.

27. The system according to claim 23 and wherein the sensor is a luminescence sensor operative to sense fluorescence.

28. The system according to claim 23 and wherein said electrical circuit includes a via formed therein, said via having a depth, wherein said luminescence sensors is positioned at an angle with respect to the via, such that said sensor can view and provide sensed information generally along the entire depth of said via.

29. The system according to claim 23 and wherein said sensor has an adjustable sensitivity.

30. The system according to claim 23 and wherein said radiation beam comprises a laser beam.

31. The system according to claim 23 and wherein said processor comprises a filter to filter out a level of luminescence which could cause a false alarm.

32. The system according to claim 23 and wherein said processor processes said information signals to produce a set of binary images with reference to at least two different predetermined detection thresholds for luminescence.

33. The system according to claim 32 wherein said processor multiplies said binary images together, and calculates a composite image.

34. The system according to claim 33 wherein said processor compares said composite image to predetermined defect parameters, and produces a defect report.

35. The system according to claim 23 and further comprising a drilling laser operative to drill a hole or via in said electrical circuit, said automated optical inspection system and said drilling laser being in electrical communication with a controller, wherein a position of the hole of via is fed from said automated optical inspection system to said controller, which instructs said drilling laser to drill the hole or via.

36. The system according to claim 35 and wherein the position of the hole or via is fed from said automated optical inspection device if said hole or via is analyzed by the processor to be defective and repairable.

37. The system according to claim 35 and wherein said drilling laser is operative to avoid drilling any holes or vias on said electrical circuit if any said hole or via on said electrical circuit is determined by said automated optical inspection system to be defective and not repairable.

38. The system according to claim 35 wherein said drilling laser comprises a $CO_2$ laser.

39. The system according to claim 38 wherein said controller is said processor.

40. The system according to claim 35 wherein said controller is said processor.

41. The system according to claim 35 wherein said drilling laser is said source of electromagnetic radiation for delivering a radiation beam on an article to be inspected.

* * * * *